(12) United States Patent
McFall

(10) Patent No.: US 11,297,887 B1
(45) Date of Patent: Apr. 12, 2022

(54) FACE MASK

(71) Applicant: Frances C. McFall, Clintwood, VA (US)

(72) Inventor: Frances C. McFall, Clintwood, VA (US)

( * ) Notice: Subject to any disclaimer, the term of this patent is extended or adjusted under 35 U.S.C. 154(b) by 0 days.

(21) Appl. No.: 17/363,909

(22) Filed: Jun. 30, 2021

(51) Int. Cl.
*A61B 19/00* (2006.01)
*A41D 13/11* (2006.01)

(52) U.S. Cl.
CPC ...... *A41D 13/1184* (2013.01); *A41D 13/1161* (2013.01)

(58) Field of Classification Search
CPC .............. A41D 13/1184; A41D 13/1161; A41D 13/11; A41D 13/1192; A61F 9/045; A61F 9/06; A45D 44/12; A45D 44/002; A61N 2005/0647; A61N 5/0616; A61N 2005/0648; A61N 5/0624; A61N 2005/063; A61N 2005/0645; A62B 23/00; A62B 23/02; A62B 23/025; A61M 16/06; A61L 9/20; A61L 9/00; A61L 2209/12
USPC .............. 128/863, 847, 205.27, 206.12
See application file for complete search history.

(56) References Cited

U.S. PATENT DOCUMENTS

| | | | |
|---|---|---|---|
| 5,165,395 A | 11/1992 | Ricci | |
| 6,029,271 A | 2/2000 | Banuchi | |
| 6,079,980 A | 6/2000 | Durand | |
| 6,901,930 B2 | 6/2005 | Henley | |
| 7,272,860 B2 | 9/2007 | Vega et al. | |
| 8,733,356 B1 | 5/2014 | Roth | |
| 9,532,617 B2 | 1/2017 | Miller et al. | |
| 11,000,624 B1* | 5/2021 | Babcock | A61L 9/20 |
| 2008/0034458 A1* | 2/2008 | Ku | A41D 1/002 2/9 |
| 2010/0076529 A1* | 3/2010 | Tucker | A61N 5/0617 607/90 |
| 2012/0172951 A1* | 7/2012 | Choi | A61N 5/0616 607/91 |
| 2016/0051835 A1* | 2/2016 | Tapper | A61N 5/0616 607/90 |
| 2017/0246076 A1* | 8/2017 | Miller | A61H 7/007 |
| 2018/0352936 A1* | 12/2018 | Kim | A45D 44/002 |
| 2020/0001107 A1* | 1/2020 | Binner | A61N 5/0616 |
| 2021/0077825 A1* | 3/2021 | Jung | A61N 5/0616 |

* cited by examiner

*Primary Examiner* — Victoria H Fisher
(74) *Attorney, Agent, or Firm* — Cramer Patent & Design, PLLC; Aaron R. Cramer

(57) ABSTRACT

A face mask is a face shield and head strap comprising two layers of plastic having a plurality of blue LED lights which are disposed about each of four face shield sides. The face mask also has a power source, power switch and plurality of air vents. When activated the plurality of blue LED lights act a sanitizer.

19 Claims, 5 Drawing Sheets

FACE MASK

RELATED APPLICATIONS

None.

FIELD OF THE INVENTION

The present invention relates generally to an article of personal protective equipment and more specifically to a face mask.

BACKGROUND OF THE INVENTION

Recent events in our history, such as the COVID-19 virus, remind us how susceptible humans are to contaminants in the air we breathe. Whether such contaminants are incidental such as dust, dirt, allergens or the like, or something more dangerous such as bacteria and viruses, many people turn to the use of face shields for protection.

While shields are available in varying sizes and designs, one common trait is that they only stop the direct impact of various unwanted contaminants whether being inhaled or exhaled. Such action allows potentially dangerous particles such as bacteria and viruses to work their way around the sides of the shield where they may infect the wearer, or those around them. Accordingly, there exists a need for a means by which biologically hazardous materials in air can be killed on the interior of a face shield. The development of the face mask fulfills this need.

SUMMARY OF THE INVENTION

To achieve the above and other objectives, the present invention provides for a face shield which has a dual layer plastic plate having a top, a bottom, a pair of sides, a lower corner, a perimeter, a foam rubber cushion which is disposed along an upper edge of the dual layer plastic plate to allow for properly positioning the face shield when worn, a pair of pivoting means that rotate the dual layer plastic plate upwards with respect to the foam rubber cushion, a Nylon strap which is adapted to secure the face shield on a user's head, a battery enclosure which is disposed on top of the foam rubber cushion to provide a battery that provides a plurality of electrical power to the face shield, a sanitizing light source which is disposed on the top, a power switch which is located on the lower corner of the dual layer plastic plate to allow for control of the sanitizing light source, a plurality of ventilation openings which are disposed around the perimeter of the dual layer plastic plate the bottom and the pair of sides of the dual layer plastic plate and, a wiring harness exiting the battery enclosure, the wiring harness includes a loop to provide adequate slack to allow the dual layer plastic plate to be raised and lowered along the rotational travel path without interference. The dual layer plastic plate serves as a protective element of the face shield and the dual layer plastic plate is pivoted upward along a rotational travel path.

The dual layer plastic plate may be rotated to perform one or more actions without interference from the dual layer plastic plate, but without totally removing the face shield via manipulation of the Nylon strap and the fastener. A plurality of ambient air may enter along the sides and the bottom of the dual layer plastic plate. The ambient air may be adapted to pass by the sanitizing light sources before entering a user's nose. The ambient air may kill one or more germs, bacteria, viruses or other contagions before they are ingested via a user. Any contagion may be expelled by the user and may be killed via the sanitizing light source as they exit the dual layer plastic plate. The pair of pivoting means may be a rivet. The Nylon strap may be secured in place via a fastener. The fastener may be a hook and loop fastener. The fastener may be adapted to size the Nylon strap to properly fit a plurality of head sizes from children to adults. The battery enclosure may include a box bottom and a box top connected by a hinge and secured by a hasp. The battery enclosure may contain a plurality of replaceable batteries. The battery enclosure may be disposed on top of the foam rubber cushion where it is secured via an adhesive. The foam rubber cushion may be secured to the Nylon strap via the adhesive.

The sanitizing light source may kill one or more germs, one or more bacteria, and one or more viruses before they are breathed in. The sanitizing light source may kill the one or more germs, the one or more bacteria, and the one or more viruses that are exhaled to allow for protection of others. The power switch position may facilitate activation and deactivation. The wiring harness may be routed into an interstitial space between an exterior panel and an interior panel of the dual layer plastic plate. The wiring harness, the sanitizing light sources, and the power switch may be disposed within the interstitial space to provide physical protection and prevent entanglement. The ventilation openings may allow air access to the interstitial space to further the contagion killing properties of the face shield.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
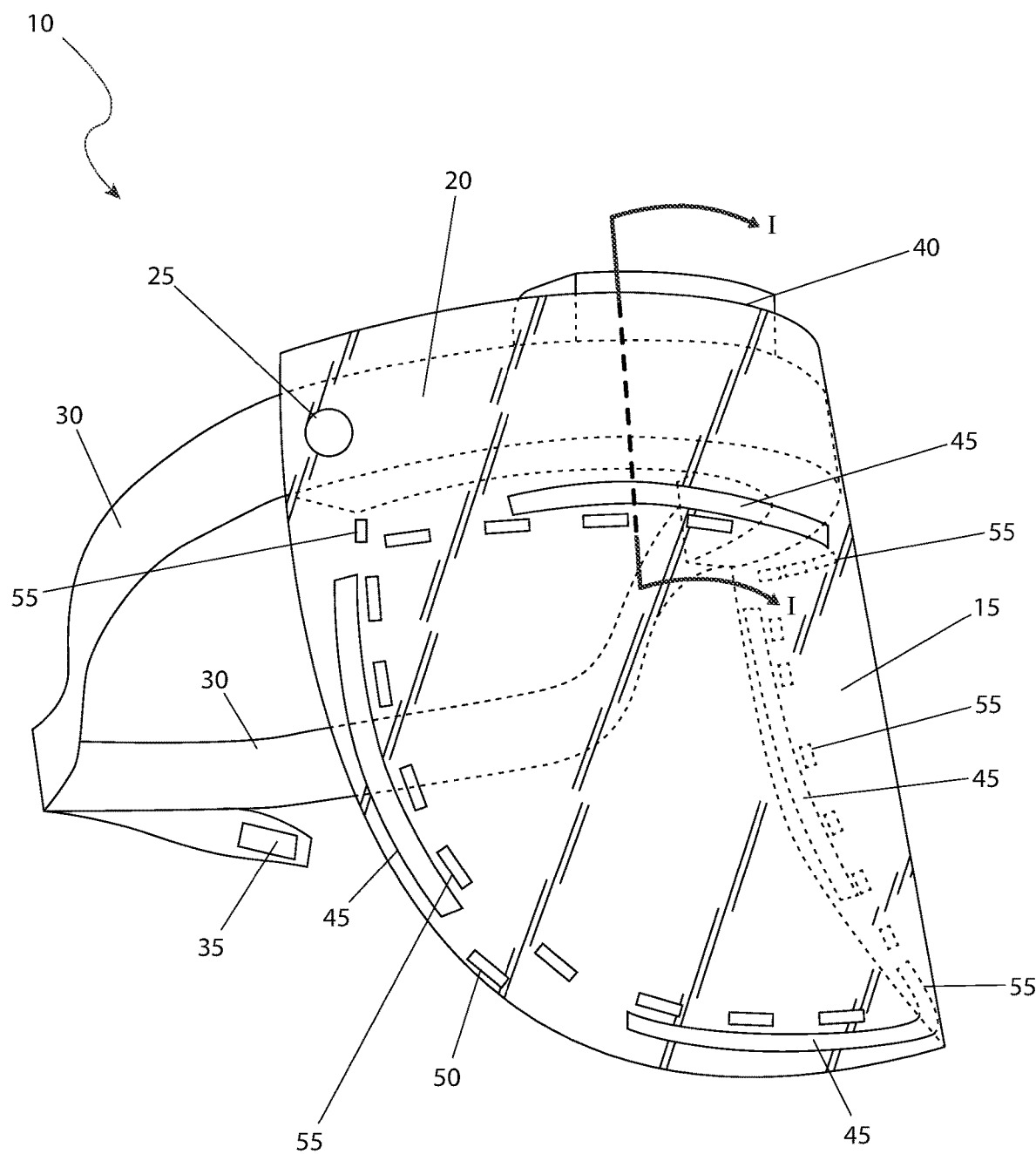
FIG. 1 is a perspective view of the face shield 10, according to the preferred embodiment of the present invention.

DESCRIPTIVE KEY 10 face shield
15 dual layer plastic plate
20 foam rubber cushion
25 pivoting means
30 nylon strap
35 fastener
40 battery enclosure
45 sanitizing light source
50 power switch
55 ventilation opening
60 user
65 face
70 rotational travel path "u"

75 ambient air
80 nose
85 mouth
90 box bottom
95 box top
100 hinge
105 hasp
110 user replaceable batteries
115 wiring harness
120 loop
125 interstitial space
130 exterior panel
135 interior panel
140 adhesive

DESCRIPTION OF THE PREFERRED EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a perspective view of the face shield 10, according to the preferred embodiment of the present invention is disclosed. The face shield (herein also described as the "face shield") 10, provides a sanitizing light source 45 that kills germs, bacteria, and viruses, before they can be breathed in or as they are exhaled to allow for protection of others. A dual layer plastic plate 15 forms the main the protective element of the face shield 10. A foam rubber cushion 20 is provided along the upper edge of the dual layer plastic plate 15 to allow for proper positioning when worn. Two (2) pivoting means 25, of which only one (1) is shown due to illustrative limitations, such as a rivet, allows the dual layer plastic plate 15 to be rotated upwards with respect to the foam rubber cushion 20, as will be shown in greater detail herein below. A nylon strap 30 secures the face shield 10 in position on a wearer's head. The nylon strap 30 is secured in place via a fastener, such as a hook-and-loop-type fastener like Velcro®. In addition to providing securement, the fastener 35 allows for sizing of the nylon strap 30 to properly fit all sizes of heads of various users from children to adults. A battery enclosure 40 is provided on top of the foam rubber cushion 20 to provide electrical power for the face shield 10. A set of four (4) sanitizing light sources 45 envisioned to be blue in color are provided on the top, bottom and sides of the dual layer plastic plate 15. A power switch 50 is located on the lower corner of the dual layer plastic plate 15 to allow for control of the sanitizing light sources 45. A plurality of ventilation openings 55 are visible around the perimeter of the dual layer plastic plate 15.

Figure 2:
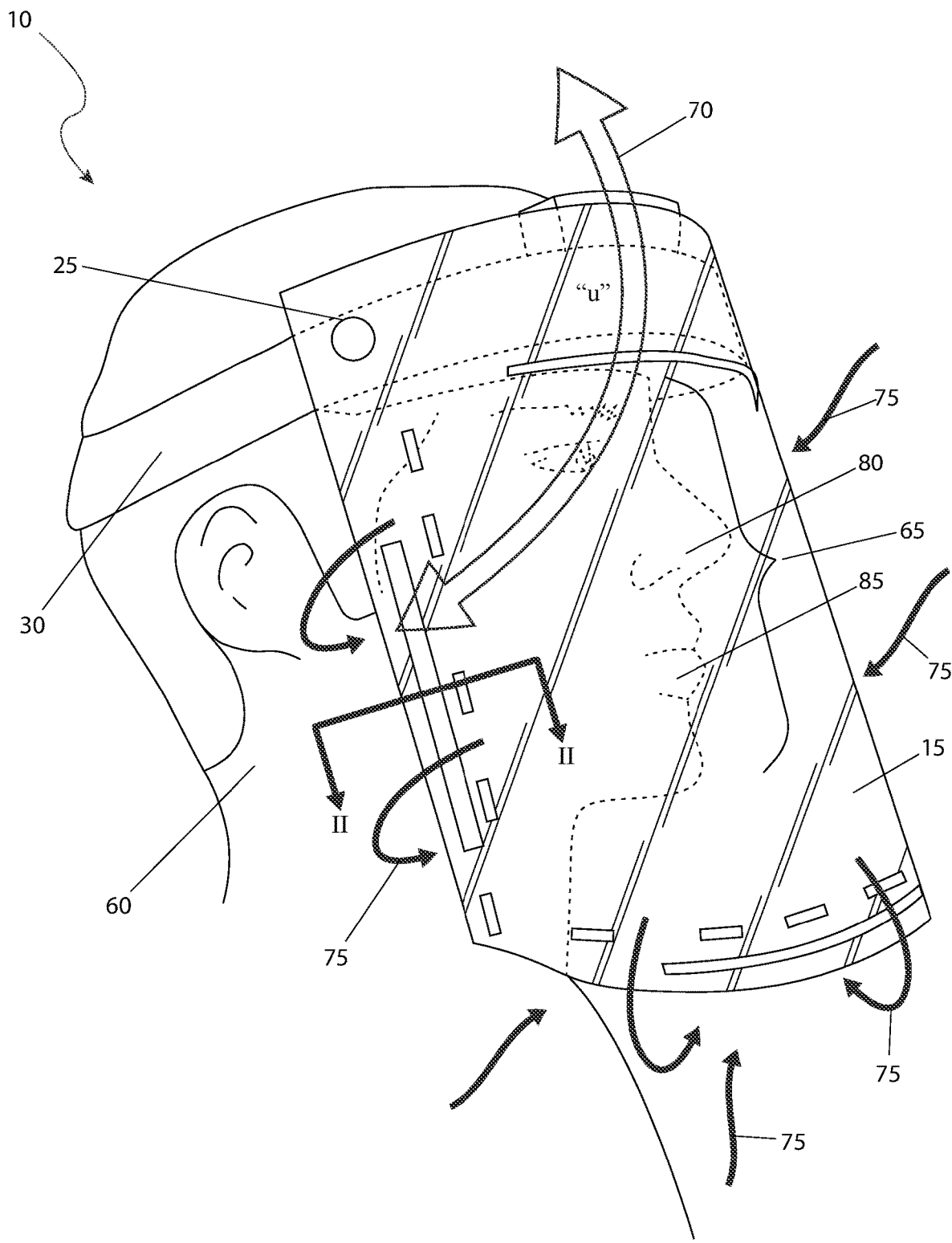
FIG. 2 is a perspective view of the face shield 10, shown in a utilized state, according to the preferred embodiment of the present invention.

Referring next to FIG. 2, a perspective view of the face shield 10, shown in a utilized state, according to the preferred embodiment of the present invention is depicted. A user 60 positions the face shield 10 over their entire face 65 in a usual, customary, and expected manner. The dual layer plastic plate 15 may be pivoted upward around the pivoting means 25 along a rotational travel path "u" 70. Said action allows the user 60 to eat, drink, utilize a telephone, or perform other actions without interference from the dual layer plastic plate 15, but without totally removing the face shield 10 via manipulation of the nylon strap 30 and fastener 35 (as shown in FIG. 1). The movement along the rotational travel path "u" 70 provides the ability to quickly transition from a down to up state thus maintaining the maximum amount of coverage time (down position) possible. Ambient air 75 can enter along the sides and bottom of the dual layer plastic plate 15. The ambient air 75 must pass by one (1) or more of the sanitizing light sources 45 before entering the nose 80 or the box top 95 of the user 60. Such action will kill any germs, bacteria, viruses or other contagions before they can be ingested via the user 60. Likewise, should the user 60 be contagious, any contagion expelled by the nose 80 or mouth 85 from the user 60 will be rendered harmless via the sanitizing light sources 45 as they exit the area of the dual layer plastic plate 15. The positioning of the power switch 50 allows for easy activation and deactivation by the user 60 as needs dictate.

Figure 3:
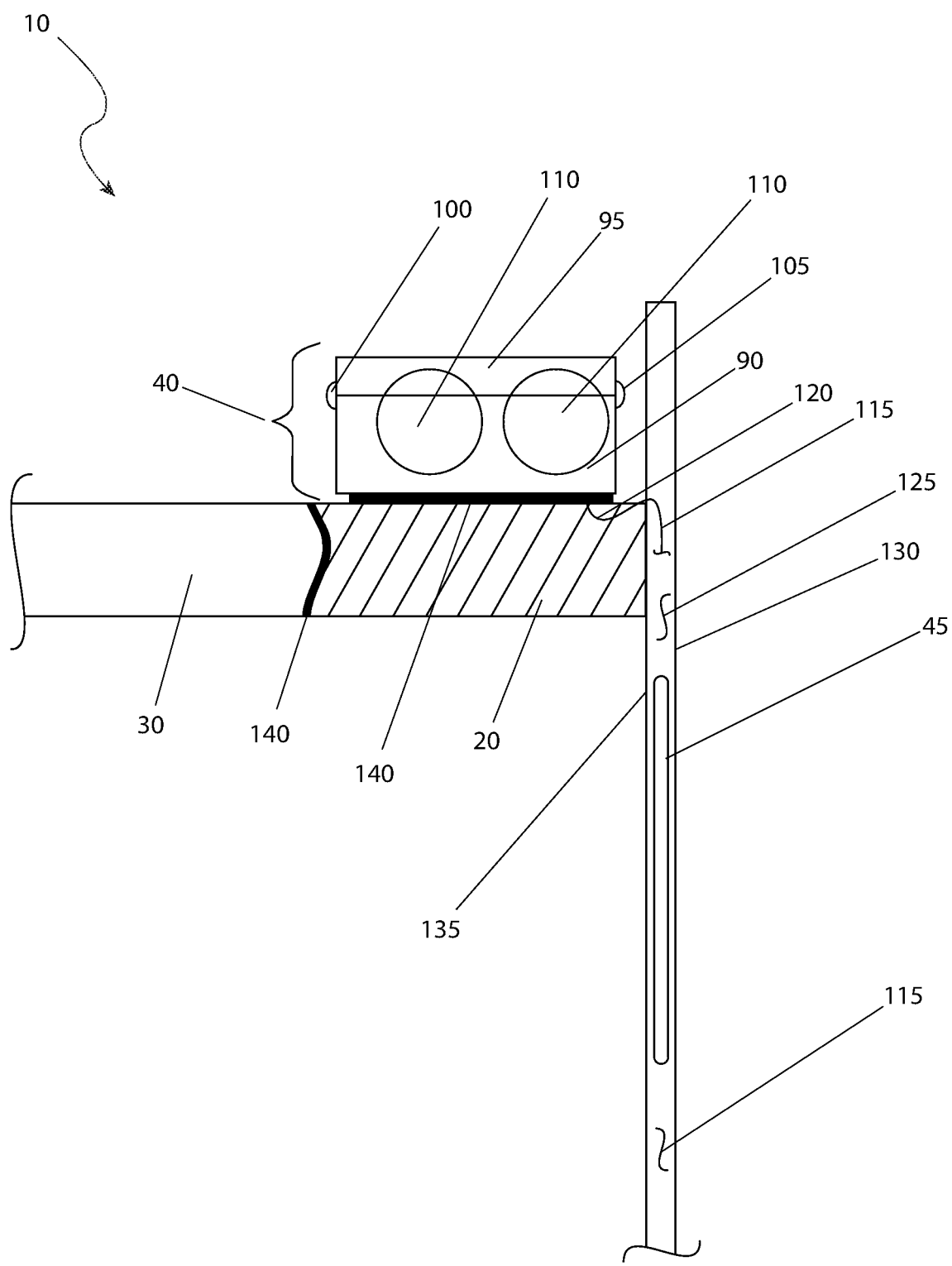
FIG. 3 is a sectional view of the face shield 10, as seen along a line I-I, as shown in FIG. 1, according to the preferred embodiment of the present invention.

Referring now to FIG. 3, a sectional view of the face shield 10, as seen along a line I-I, as shown in FIG. 1, according to the preferred embodiment of the present invention is shown. The battery enclosure 40 includes a box bottom 90 and a box top 95 connected by a hinge 100 and secured by a hasp 105. At least two (2) user replaceable batteries 110 such as AA batteries are provided inside. A wiring harness 115 exits the battery enclosure 40 and is provided with a loop 120 to provide adequate slack to allow the dual layer plastic plate 15 to be raised and lowered along the rotational travel path "u" 70 as shown in FIG. 2 without interference. The wiring harness 115 is routed into an interstitial space 125 between an exterior panel 130 and an interior panel 135 comprising the dual layer plastic plate 15. The wiring harness 115 is routed to the sanitizing light sources 45 and the power switch 50 (as shown in FIG. 1) as required. The placement of the wiring harness 115, the sanitizing light sources 45, and the power switch 50 within the interstitial space 125 provides physical protection and prevents entanglement with clothing, tools, conventional fabric face masks and the like. The battery enclosure 40 is positioned on top of the foam rubber cushion 20 where it is secured via adhesive 140. Similarly, the foam rubber cushion 20 is secured to the nylon strap 30 via adhesive 140 as well.

Figure 4:
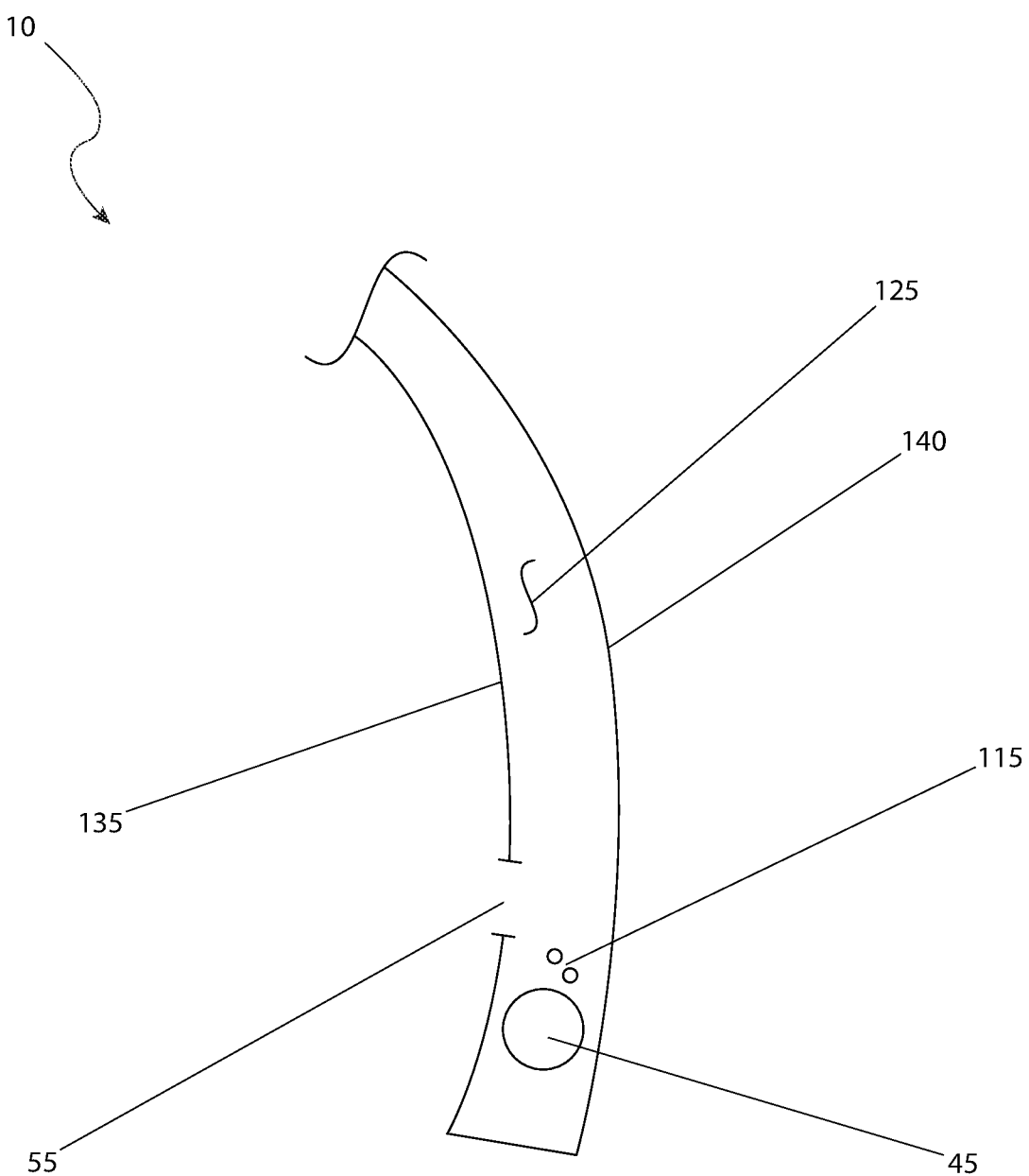
FIG. 4 is a sectional view of the face shield 10, as seen along a line II-II, as shown in FIG. 2, according to the preferred embodiment of the present invention; and, FIG. 5 is an electrical block diagram of the face shield 10, according to the preferred embodiment of the present invention.

Referring next to FIG. 4, a sectional view of the face shield 10, as seen along a line II-II, as shown in FIG. 2, according to the preferred embodiment of the present invention is disclosed. This view provides an alternate view of the interstitial space 125 from an angle of ninety-degrees (90°) to that provided in FIG. 3. The interstitial space 125 houses the sanitizing light sources 45 along with the wiring harness 115 as it travels from the battery enclosure 40 (as shown in FIGS. 1 and 3) to other sanitizing light sources 45 and/or the power switch 50. Additionally, one (1) of the multiple ventilation openings 55 on the interior panel 135 are visible. The ventilation openings 55 allows air access to the interstitial space 125 to further the contagion killing properties of the face shield 10.

Figure 5:
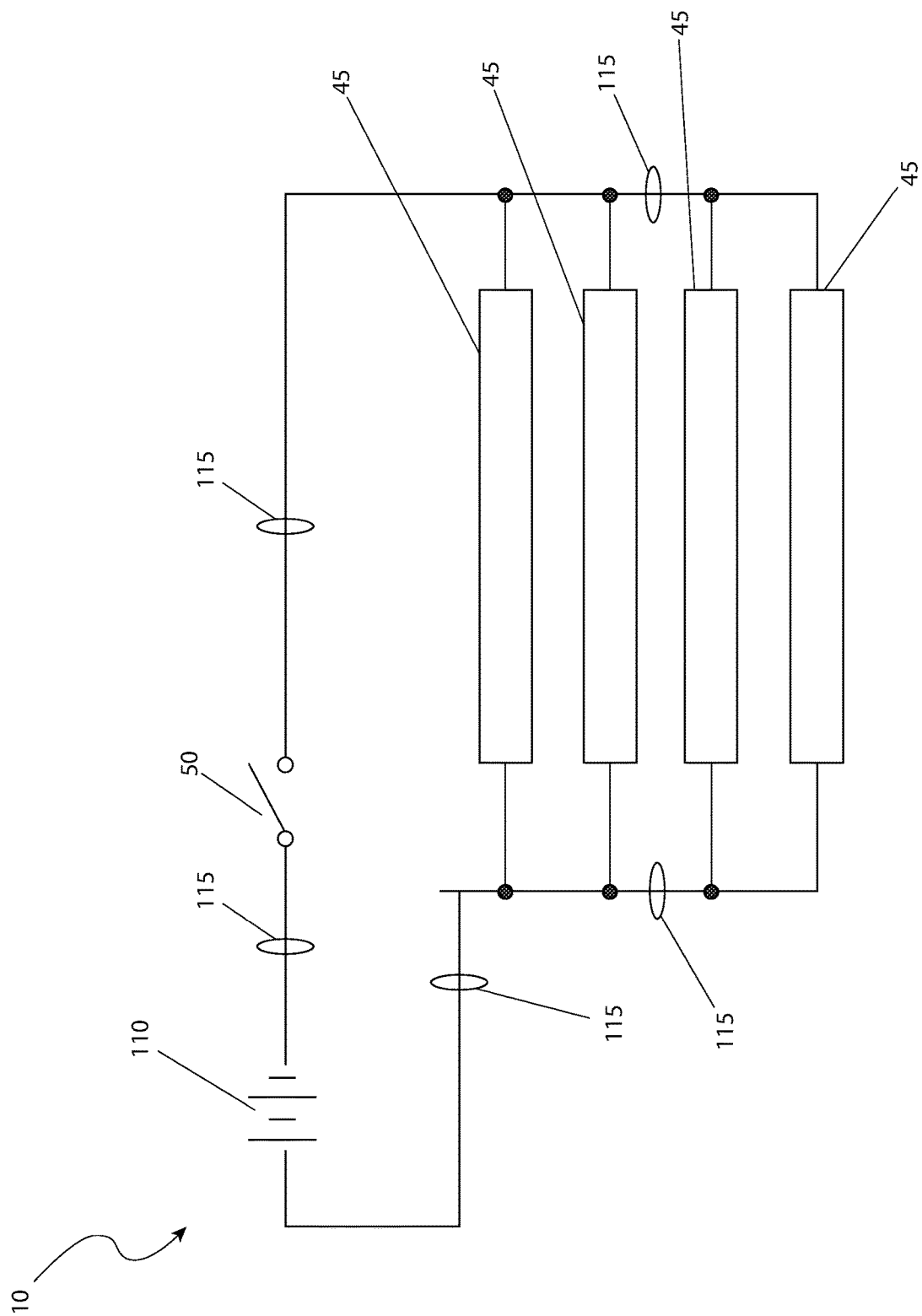

Referring to FIG. 5, an electrical block diagram of the face shield 10, according to the preferred embodiment of the present invention is depicted. Electrical power from the user replaceable batteries 110 is routed in a series fashion with the power switch 50 via the wiring harness 115. The load side of the power switch 50 is then routed to the four (4) sanitation light sources 45 which are wired in parallel with one (1) another, once again via the wiring harness 115. The series circuit is then closed with a return path the user replaceable batteries 110 via the wiring harness 115.

2. Operation of the Preferred Embodiment

The preferred embodiment of the present invention can be utilized by the common user in a simple and effortless manner with little or no training. It is envisioned that the face shield 10 would be constructed in general accordance with FIG. 1 through FIG. 5. The user would procure the face shield 10 from conventional procurement channels such as medical supply houses, discount stores, department stores, drug stores, mail order and internet supply houses and the like.

After procurement and prior to utilization, the face shield 10 would be prepared in the following manner: user replaceable batteries 110 would be placed within the box bottom 90 of the battery enclosure 40; the box top 95 would be closed along the hinge 100 and secured with the hasp 105; and proper operation of the sanitizing light sources 45 would be verified via activation of the power switch 50. At this point in time, the face shield 10 is ready for use.

During utilization of the face shield 10, the following procedure would be initiated: the user would apply the foam rubber cushion 20 to their forehead area as shown in FIG. 2; the nylon strap 30 would be sized to ensure a tight but comfortable fit; the fastener 35 would be used to secure the nylon strap 30 onto itself; and the dual layer plastic plate 15 would be lowered into position over the face 65 of the user 60 and the power switch 50. This action will ensure that any germs, bacteria, viruses or other contagions will be killed or neutralized by the sanitizing light sources) 45 prior to entering or after exiting the nose 80 or the mouth 85 of the user 60. Should other activities, such as eating, drinking, or the like need to occur, the user 60 would deactivate the power switch 50 and raise the dual layer plastic plate 15 in a manual manner along the rotational travel path "u" 70.

After use of the face shield 10, it is removed via manipulation of the fastener 35 and the face shield 10 removed from the face 65 of the user 60. The exterior panel 130 and the interior panel 135 may be wiped clean and the face shield 10 stored until needed again in a repeating manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A face shield, comprising:
    a dual layer plastic plate having a top, a bottom, a pair of sides, a lower corner, a perimeter, the dual layer plastic plate serving as a protective element of the face shield and the dual layer plastic plate is capable of being pivoted upward along a rotational travel path;
    a foam rubber cushion disposed along an upper edge of the dual layer plastic plate to allow for properly positioning the face shield when worn;
    a pair of pivoting means capable of rotating the dual layer plastic plate upwards with respect to the foam rubber cushion;
    a Nylon strap adapted to secure the face shield on a user's head;
    a battery enclosure disposed on top of the foam rubber cushion to provide a battery that provides a plurality of electrical power to the face shield;
    a sanitizing light source disposed on the top, the bottom and the pair of sides of the dual layer plastic plate;
    a power switch located on the lower corner of the dual layer plastic plate to allow for control of the sanitizing light source;
    a plurality of ventilation openings disposed around the perimeter of the dual layer plastic plate; and
    a wiring harness exiting the battery enclosure, the wiring harness includes a loop to provide adequate slack to allow the dual layer plastic plate to be raised and lowered along the rotational travel path without interference.

2. The face shield, according to claim 1, wherein the dual layer plastic plate is capable of being rotated to perform one or more actions without interference from the dual layer plastic plate, but without totally removing the face shield via manipulation of the Nylon strap and a fastener.

3. The face shield, according to claim 1, wherein a plurality of ambient air is capable of entering along the pair of sides and the bottom of the dual layer plastic plate.

4. The face shield, according to claim 3, wherein the plurality of ambient air is adapted to pass by the sanitizing light sources before entering the user's nose.

5. The face shield, according to claim 3, wherein the plurality of ambient air is capable of killing one or more germs, bacteria, viruses or other contagions before they are ingested via a user.

6. The face shield, according to claim 4, wherein any contagion expelled by the user is capable of being killed via the sanitizing light source as they exit the dual layer plastic plate.

7. The face shield, according to claim 3, wherein the pair of pivoting means is a rivet.

8. The face shield, according to claim 1, wherein the Nylon strap is secured in place via a fastener.

9. The face shield, according to claim 8, wherein the fastener is a hook and loop fastener.

10. The face shield, according to claim 8, wherein the fastener is adapted to size the Nylon strap to properly fit a plurality of head sizes from children to adults.

11. The face shield, according to claim 1, wherein the battery enclosure includes a box bottom and a box top connected by a hinge and secured by a hasp.

12. The face shield, according to claim 1, wherein the battery enclosure contains a plurality of replaceable batteries.

13. The face shield, according to claim 1, wherein the battery enclosure is disposed on top of the foam rubber cushion where it is secured via an adhesive.

14. The face shield, according to claim 13, wherein the foam rubber cushion is secured to the Nylon strap via the adhesive.

15. The face shield, according to claim 1, wherein the sanitizing light source is capable of killing one or more germs, one or more bacteria, and one or more viruses before they are breathed in.

16. The face shield, according to claim 15, wherein the sanitizing light source is capable of killing the one or more germs, the one or more bacteria, and the one or more viruses that are exhaled to allow for protection of others.

17. The face shield, according to claim 1, wherein a position of the power switch facilitates activation and deactivation.

18. The face shield, according to claim 1, wherein the wiring harness is routed into an interstitial space between an exterior panel and an interior panel of the dual layer plastic plate.

19. The face shield, according to claim 18, wherein the plurality of ventilation openings allows air access to the interstitial space to further the contagion killing properties of the face shield.

\* \* \* \* \*